(12) United States Patent
Dunlap

(10) Patent No.: US 7,100,612 B2
(45) Date of Patent: Sep. 5, 2006

(54) NASOPHARYNGEAL AIRWAY DEVICE AND METHOD OF USE

(75) Inventor: Ivan L. Dunlap, St. George, UT (US)

(73) Assignee: EPIC Corporation, St. George, UT (US)

(*) Notice: Subject to any disclaimer, the term of this patent is extended or adjusted under 35 U.S.C. 154(b) by 0 days.

(21) Appl. No.: 10/936,940

(22) Filed: Sep. 9, 2004

(65) Prior Publication Data
US 2006/0048775 A1 Mar. 9, 2006

(51) Int. Cl.
A61M 15/08 (2006.01)

(52) U.S. Cl. ............... 128/207.18; 128/206.11; 128/200.06

(58) Field of Classification Search .......... 128/200.26, 128/206.28, 207.13, 207.18, 898, 858, 206.11; 606/196, 199, 204.45; D24/106
See application file for complete search history.

(56) References Cited

U.S. PATENT DOCUMENTS

| 2,822,809 | A |  | 2/1958 | Sollmann |  |
| 3,568,678 | A | * | 3/1971 | Pourquier et al. | 604/174 |
| 4,402,684 | A |  | 9/1983 | Jessup |  |
| 5,664,567 | A |  | 9/1997 | Linder |  |
| 5,937,858 | A |  | 8/1999 | Connell |  |
| 6,328,753 | B1 |  | 12/2001 | Zammit |  |
| 6,789,538 | B1 | * | 9/2004 | Wright et al. | 128/200.26 |
| 2003/0136413 | A1 | * | 7/2003 | Brain et al. | 128/207.15 |

* cited by examiner

Primary Examiner—Henry Bennett
Assistant Examiner—Shumaya B. Ali
(74) Attorney, Agent, or Firm—Workman Nydegger (57) ABSTRACT

A nasopharyngeal airway device has a tubular body with a securement assembly disposed at the proximal end thereof. The tubular body may include a plurality of apertures along the sidewall thereof. The securement assembly can include a flared flange and an outwardly extending locking protrusion. During use, the tubular body is positioned within the nasal passageway. The locking protrusion is bent and also inserted into the nasal passageway so as to secure the nasopharyngeal airway device in place.

30 Claims, 6 Drawing Sheets

NASOPHARYNGEAL AIRWAY DEVICE AND METHOD OF USE

CROSS-REFERENCE TO RELATED APPLICATIONS

Not applicable.

BACKGROUND OF THE INVENTION

1. The Field of the Invention

The present invention relates to nasopharyngeal airway devices and their methods of use.

2. The Relevant Technology

The medical industry uses nasopharyngeal airway devices to assist a patient in breathing. A typical nasopharyngeal airway devices comprises an elongated tube having an opening located at the top end and at the bottom end so that air can pass therethrough. The devices is inserted into one of the nasal passageways of the patient, thereby providing an unobstructed passageway through which the patient can easily breath. For example, nasopharyngeal airway devices are commonly used in patients who are still under anesthesia following an operation and who may have some difficultly breathing. Once the patient is fully awake, the device can be removed.

An enlarged circular flange is located at the first end of the nasopharyngeal airway device so as to prevent the device from being slid too far into the nasal passageway of the patient. Natural movements of the patient, however, often causes the device to progressively slide out of the nasal cavity. As such, the medical staff must be continually vigilant to ensure that the nasopharyngeal airway device is continually retained within the nasal passageway so as to ensure proper breathing. This unwanted movement of the nasopharyngeal airway device not only creates risk to the patient'S breathing but the continued reinsertion of the device can further irritate the lining of the nasal passageway.

It is appreciated that there are other additional shortcomings associated with conventional nasopharyngeal airway devices. For example, as a person breathes through their nose, humidity in the surrounding air provides moisture to the lining of the nasal passageway. By inserting the nasopharyngeal airway device into the nasal passageway, the air is no longer passing over the lining of the nasal passageway but is rather passing through the device. As a result, the nasopharyngeal airway device can result in drying out of the nasal passageway which in turn can cause irritation of the lining and/or nose bleeds.

Furthermore, sinus and other bodily fluids are continually delivered to the nasal passageway. These fluids typically flow back and down the throat of the patent. However, because conventional nasopharyngeal airway devices only have a single opening at the second end thereof, there is the potential risk that the single opening can become constricted or occluded by the fluids, thereby limiting that ability of the patient to breath through nasopharyngeal airway devices.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention is directed to nasopharyngeal airway devices that are selectively inserted within a nasal passageway of a patient and can be used for various purposes. For example, the devices are commonly used on patients coming out of anesthesia after an operation to provide them with an open airway through which they can easily breathe. The inventive nasopharyngeal airway devices can also be used to assist individuals with breathing who experience sleep apnea. Other potential uses for the device include, but are not limited to, administering anesthesia, administering nutrients or feedings, resuscitation, and the like.

Figure 1:
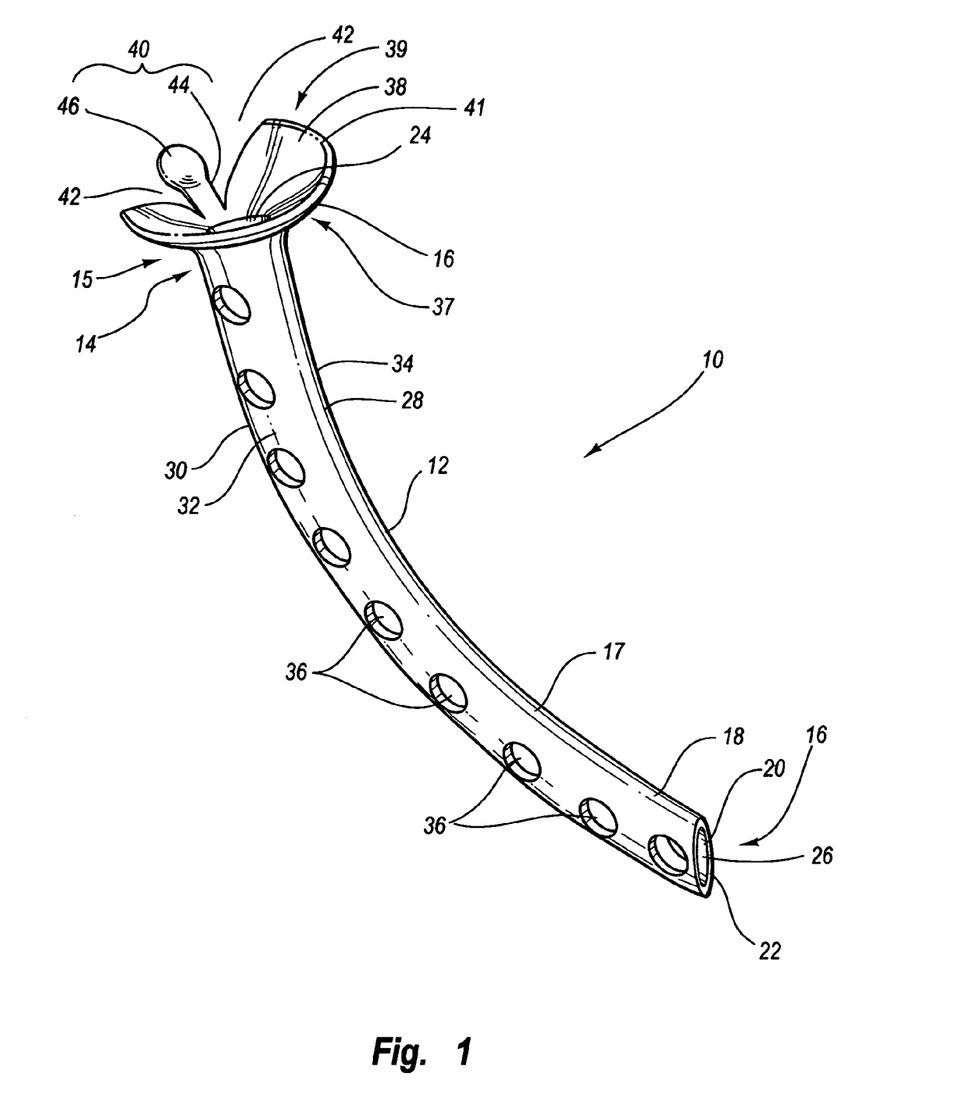
FIG. 1 is a perspective view of one embodiment of a nasopharyngeal airway device.

Depicted in FIG. 1 is one embodiment of a nasopharyngeal airway device 10 incorporating features of the present invention. Device 10 includes an elongated tubular body 12 in the form of a tube having a proximal end 14 and an opposing distal end 16. Tubular body 12 includes a sidewall 17 having an exterior surface 18 and an interior surface 20 extending between proximal end 14 and distal end 16. In one embodiment distal end 16 is tapered to facilitate easy insertion. Interior surface 20 bounds an air passage 22. Air passage 22 extends between proximal end 14 and distal end 16 of tubular body 12. Air passage 22 communicates with an opening 24 formed at proximal end 14 of tubular body 12 and an opening 26 formed at distal end 16 of tubular body 12. Air passage 22 is configured to allow air to freely pass between proximal end 14 and distal end 16 of tubular body 12. It is also envisioned that air passage 22 can be configured to receive feeding tubes or other tubes to deliver medications, other gases or the like.

Tubular body 12 is comprised of a soft, flexible material so as to minimize any irritation or trauma during insertion and use. The material should also be sterilizable. Suitable materials include rubber, biocompatible plastics such as silicone, organic plastic, and other polymeric materials. For example, soft polyvinyl chloride may be used.

Tubular body 12 is depicted with exterior surface 18 and interior surface 20 each having a substantially circular transverse cross section. In alternative embodiments, however, exterior surface 18 and/or interior surface 20 can have a transverse cross section that is elliptical, polygonal, irregular, or any other desired shape.

Furthermore, in the embodiment depicted in FIG. 1, tubular body 12 is curved along the length thereof. This curvature generally complements the natural curvature of the nasal passageway and provides for easy insertion and retention of tubular body 12 within the nasal passageway. In alternative embodiments, it is appreciated that because tubular body 12 is flexible, it can also be linear or have other configurations.

Nasopharyngeal airway device 10 and tubular body 12 thereof can be formed having a variety of different sizes and configurations to accommodate different uses and different sizes of people. By way of illustration and not by limitation, in one embodiment air passage 22 can have a diameter in a range between about 5 mm to about 15 mm. The thickness of sidewall 17 of tubular body 12 is typically in a range from about 1 mm to about 3 mm. The length from proximal end 14 of tubular body 12 to distal end 16 of tubular body 12 is typically from about 10 cm to about 20 cm. Again, however, it is appreciated that other dimensions of tubular body 12 may be used depending on the intended purpose for which device 10 is used.

Figure 3:
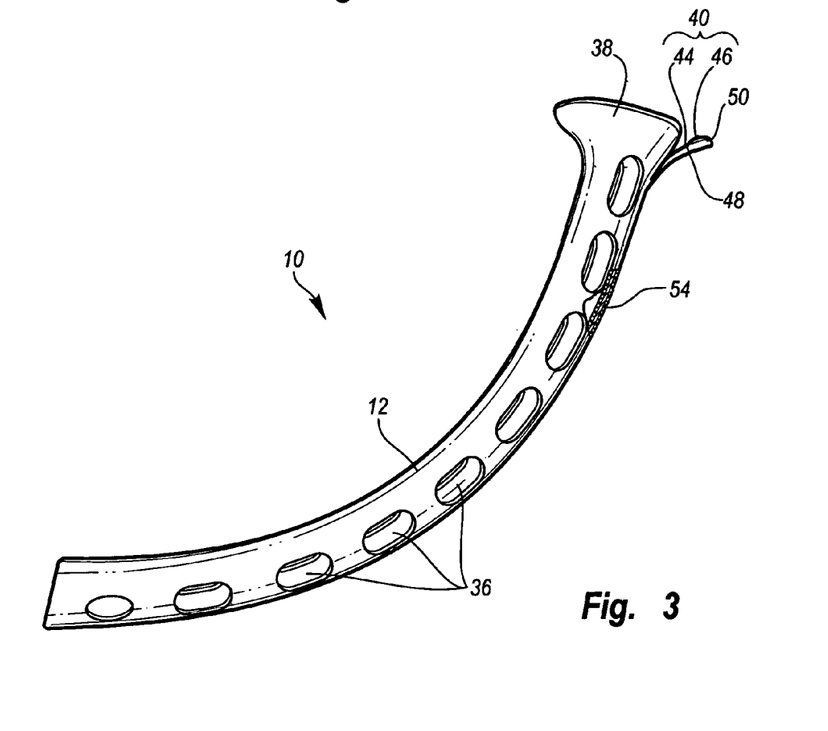
FIG. 3 a side view of the embodiment of FIG. 1.

Tubular body 12 can also be referenced as having a relative front side 28, a back side 30, a left side 32, and a right side 34. Front side 28 and back side 30 are disposed within the plane of curvature. Although not required, in one embodiment sides 32, 34 of tubular body 12 included a plurality of apertures 36 formed along the sidewall 17 of tubular body 12 so as to communicate with air passage 22. Apertures 36 can be formed at regular or irregular intervals along sidewall 17 of tubular body 12. It is also appreciated that apertures 36 can be formed on various regions of front side 28, back side 30 or can extend between various faces. It is also appreciated that apertures 36 can be any desired size, shape or configuration. For example, in contrast to being circular as shown in FIG. 1, the apertures 36 can be elongated as shown in FIG. 3.

Figure 6:
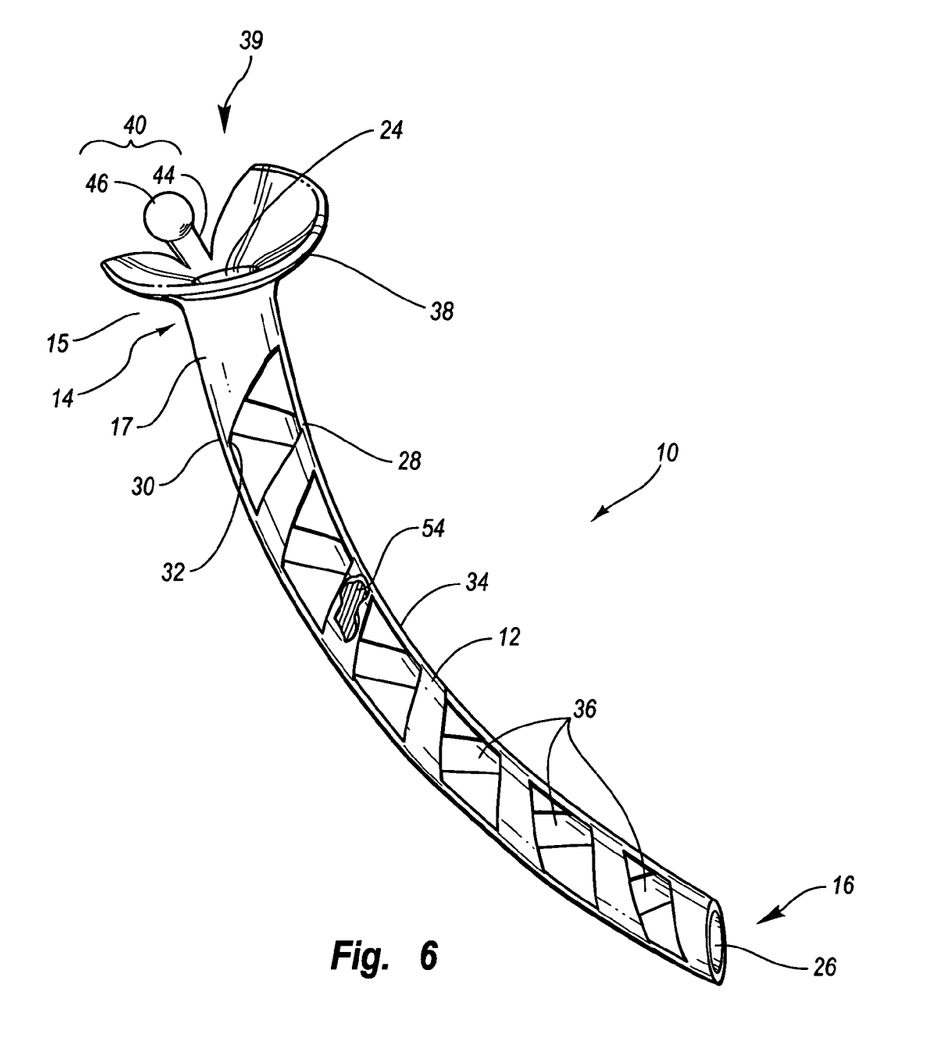

Apertures 36 allow air passing through air passage 22 to contact the lining of the nasal passageway. In turn the air helps to humidify the lining, thereby minimizing drying, irritation and cracking. In addition, by increasing the number of apertures 36 along device 10, the chance that air passage 22 will be constricted or occluded by bodily fluids decreases. For example, in one embodiment, such as depicted in FIG. 6, the number and placement of apertures 36 can be maximized so as to maximize the free flow of air through and around device 10. However, a sufficient portion of the structure of tubular body 12 is retained to prevent collapse of tubular body 12. In one embodiment, at least ⅓ of the surface area of the exterior surface of tubular body 12 comprises apertures 36. Alternatively, at least ½ of the surface area of the exterior surface of tubular body 12 comprises apertures 36. Other proportions can also be used. It is likewise appreciated that tubular body 12 can be formed without any apertures extending through sidewall 17. In this embodiment, air passage 22 only communicates with openings 24 and 26.

Returning to FIG. 1, a securement assembly 37 is disposed at the proximal end 14 of tubular body 12. In one exemplary embodiment, securement assembly 37 includes a flared flange 38 and a flexible locking protrusion 40 separated from the flared flange 38 by spaces 42. Flared flange 38 has a distal end 15 connected to tubular body 12 and an opposing proximal end 39. Proximal end 39 terminates at a perimeter edge 41. Flange 38 outwardly projects generally from front side 28, left side 32, and right side 34 of tubular body 12 while protrusion 40 generally projects from back side 30 of tubular body 12. In the embodiment depicted, flange 38 outwardly slopes from tubular body 12. In alternative embodiments, flange 38 can outwardly project normal to tubular body 12.

At at least perimeter edge 41, flange 38 has a size that is larger than the nostril opening leading to the nasal passageway for which the nasopharyngeal airway device 10 is intended to be used. Expressed in other terms, flange 38 is sufficiently sized and/or shaped so as to prevent flange 38 from freely passing into nasal passageway. As a result, flange 38 prevents device 10 from sliding back too far into the nasal passageway where it may become lodged or difficult to remove.

In one embodiment, perimeter edge 41 of flange 38 is slightly curved inward toward proximal end 39 so that the rounded edges prevent any trauma to the soft tissue. The diameter at perimeter edge 41 of flared flange 38 is typically in a range from about 2 cm to about 5 cm, although this may differ depending on the intended use of device 10. At distal end 15 of flared flange 38, the inner diameter can correspond to the inner diameter of passageway 22 of tubular body 12. The wall of flared flange 38 can have the same thickness as sidewall 17 of tubular body 12. Alternatively, the wall of flange 38 can be tapered or otherwise vary in shape and can have a different thickness than tubular body 12.

Flange 38 is also typically made of a soft, flexible material such as that discussed above with regard to tubular body 12. Flange 38 can be integrally molded with tubular body 12 or can be connected thereto such as by welding, adhesive, mechanical fastener, or the like.

As will be discussed below in greater detail, flange 38 can come in a variety of different configurations. For example, flange 38 can be designed to encircle a portion of tubular body 12 as show in FIGS. 1 and 2 or can encircle all of tubular body 12 so as to have a flat disk or frustoconical shape. In yet other embodiments, flange 38 can comprises a plurality of spaced apart flanges.

Figure 2:
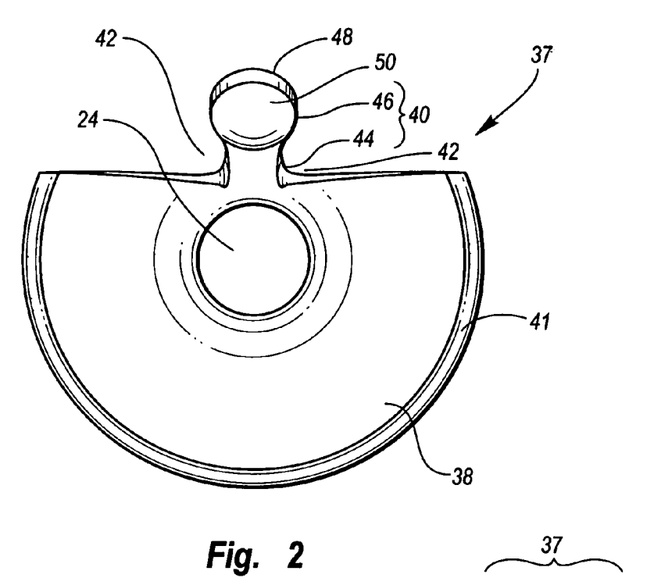
FIG. 2 is a top view of the embodiment of FIG. 1.

As also shown in FIGS. 1 and 2, locking protrusion 40 includes a stem 44 extending outwardly from proximal end 14 of tubular body 12 and terminating at a tip 46. Stem 44 can be integrally formed with or discretely connected to flared flange 38 or tubular body 12. In either case, stem 44 projects outwardly from proximal end 14 of tubular body 12 so that it functions to secure device 10 within the nasal passageway.

Figure 4:
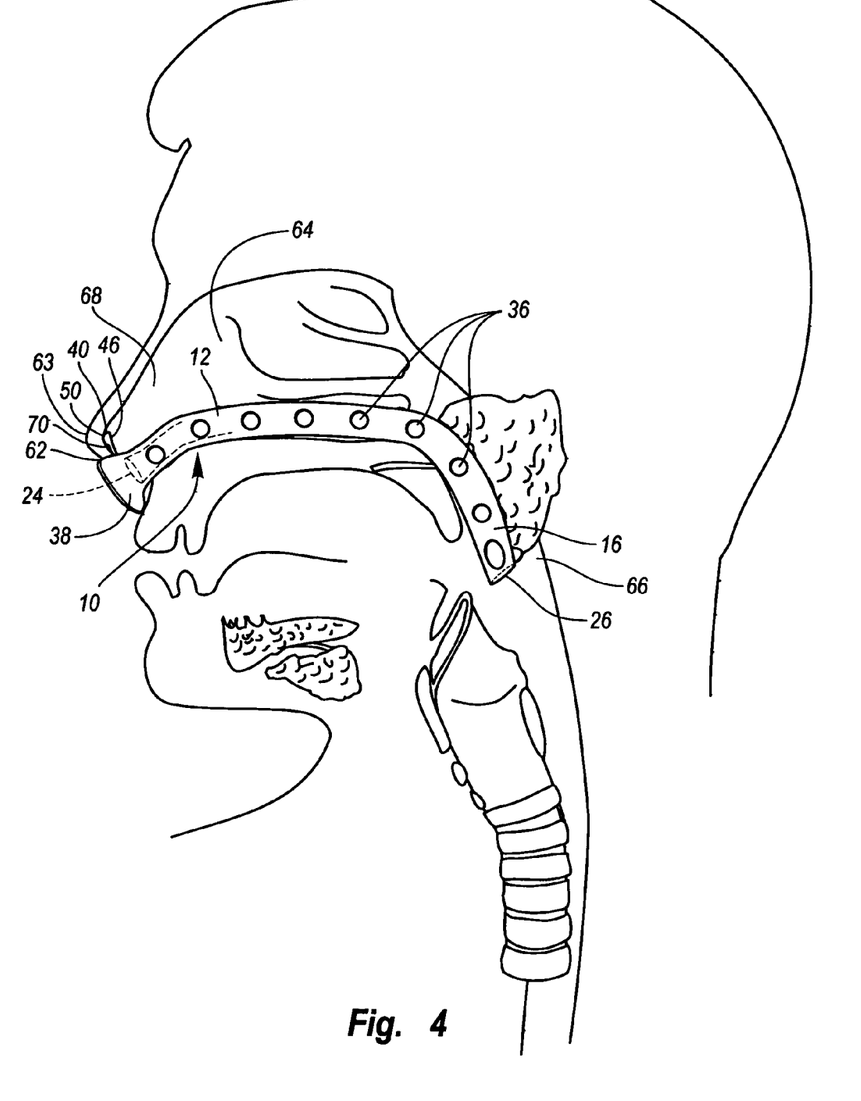
FIG. 4 a schematic view of the nasopharyngeal airway device of FIG. 1 inserted into a nasal passageway of a patient.

Specifically, during use, as depicted in FIG. 4, distal end 16 of tubular body 12 is advanced through a nostril opening 62 of a nose 63 and through a nasal passageway 64 until distal end 16 reaches an oropharynx 66. Nasal passageway 64 is bounded by lining 68. In this position, flange 38 is disposed adjacent to or against nostril opening 62. Again, flange 38 is larger than nostril opening 62 so that flange 38 cannot unintentionally slide into nasal passageway 64. In this position, opening 24 of nasopharyngeal airway device 10 communicates with the atmosphere while opening 26 communicates with oropharynx 66. As previously discussed, distal end 16 of tubular body 12 can be tapered at an angle so as to minimize trauma to lining 68 of nasal passageway 64 during insertion of device 10. In another embodiment, not shown, distal end 16 is rounded so as to minimize trauma during insertion of device 10. In one embodiment, a water based lubricant, such as Xylocaine® can be placed on distal end 16 of tubular body 12 to lubricate and/or anesthetize lining 68 of nasal passageway 64.

Once device 10 is disposed within nasal passageway 64, stem 44 of locking protrusion 40 is bent back toward distal end 16 and tip 46 is inserted within nostril opening 62 of nasal passageway 64. Locking protrusion 40 resiliently biases against lining 68 of nasal passageway 64 so as to secure device 10 within nasal passageway 64. Specifically, a recessed pocket 70 is formed within nasal passageway 64 at the tip of nose 63. Locking protrusion 40 is typically positioned on nasopharyngeal airway device 10 so as to catch within pocket 70. Opposing restraints are then used to secure device 10 in place. That is, flange 30 biases against the exterior surface of nose 63 or the lining of nasal opening 61 so as to prevent device 10 from further sliding into nasal passageway 64 while locking protrusion 40 biases against the lining of pocket 70 so as to prevent device 10 from unintentionally sliding out of nasal passageway 64. Accordingly, in the embodiment depicted in FIG. 4, locking protrusion 40 is configured such that at least the tip of locking protrusion 40 is disposed within the same nostril of the nasal passageway 64 as the nostril in which tubular body 12 is disposed when tubular body 12 is disposed within nasal passageway 64 and at least a portion of flange 30 is disposed outside of nasal passageway 64.

Locking protrusion 40 is typically formed from a flexible or semi-flexible material so that stem 44 can be bent backwards so as to place tip 46 in contact with lining 68 of nasal passageway 64. At the same time, locking protrusion 40 is sufficiently resilient to securely maintain device 10 within nasal passageway 64. In contrast to being resiliently flexible, locking protrusion 40 can be rigidly flexible. In this embodiment, once tip 46 is positioned within nasal passageway 64, locking protrusion 40 can be physically bent to catch against pocket 70.

In one embodiment, locking protrusion 40 can be constructed from the same types of materials as discussed above with regard to tubular body 12. However, for a discrete device 10, locking protrusion 40 can be made of the same material as tubular body 12 or a different material. It is also appreciated that locking protrusion 40 can be comprised of multiple materials. For example, locking protrusion 40 can comprise a base portion that is integrally formed with and made of the same material as tubular body 12. Locking protrusion 40 can further comprises a coating over the base portion made of a softer material such as a polymeric foam.

Locking protrusion 40 can be integrally formed with tubular body 12 and/or flange 38 such as by molding or other manufacturing processes. Alternatively, locking protrusion can be connected to flange 38 and/or tubular body 12 by co-molding, adhesive, welding, mechanical attachment or other means for securing.

FIGS. 2 and 3 further illustrate that tip 46 can have a relatively flat back side 48 and a rounded contact side 50. As contact side 50 is configured to contact lining 68 of nasal passageway 64, rounding of contact side 50 helps to minimize an trauma. Since the back side 48 of tip 46 generally does not contact lining 68, it is not necessary for back side 48 to be rounded, although in some embodiments it can be. In yet another embodiment, shown more clearly in FIG. 6, tip 46 can form a rounded ball.

In one embodiment, stem 44 can be integrally formed with tip 46. In another embodiment, tip 46 can be formed from a different or softer material than stem 44. For example, tip 46 could comprise a foam, rubber, or plastic or other polymeric material which is adhered to the stem 44 such as by adhesive, welding, coating, or other bonding techniques.

In typical embodiments, locking protrusion 40 has a length in a range from about 0.5 cm to about 2 cm. However, depending on the size of the patient, the size of locking protrusion 40 may vary. Ideally, the length of locking protrusion 40 is of sufficient length so that locking protrusion 40 can be easily and comfortably positioned within nasal passageway 64 and securely bias against lining 68.

As mentioned above, different materials can be used to form different elements of device 10. For example, securement assembly 37 may be formed from a slightly harder plastic than tubular body 12. Likewise, locking protrusion 40 may need to be a somewhat stiffer material than the rest of device 10 in order to securely fix device 10.

In contrast to varying stiffness by using different materials, stiffness or flexibility can also be varied by using reinforcing members. Turning back to FIG. 3, a reinforcing member 54 is embedded within and longitudinally extends along tubular body 12 and locking protrusion 40. Reinforcing member provides increased rigidity to locking protrusion 40. In contrast to being embedded, it is appreciated that reinforcing member can be placed along interior surface 20 or exterior surface 18. In one embodiment, reinforcing member 54 is in the form of an elongate rib. In other embodiments, reinforcing member 54 can comprise one or more filaments, strands, cords, lines, or the like.

It will be appreciated that reinforcing material can also be disposed on one or more of front side 28, back side 30, left side 32 and/or right side 34 and can be disposed linearly, transversely, or spirally along nasopharyngeal airway device 10 or parts thereof. For example, depicted in FIG. 6 reinforcing member 54 is spirally embedded within tubular body 12 so as to reinforce tubular body 12, thereby enabling easy insertion and preventing collapse. The reinforcement members 54 can comprised of plastic, rubber or other polymeric materials having different stiffness, sizes, and forms. In one embodiment, reinforcement members 54 can be co-molded or co-extruded with nasopharyngeal airway device 10.

Figure 5:
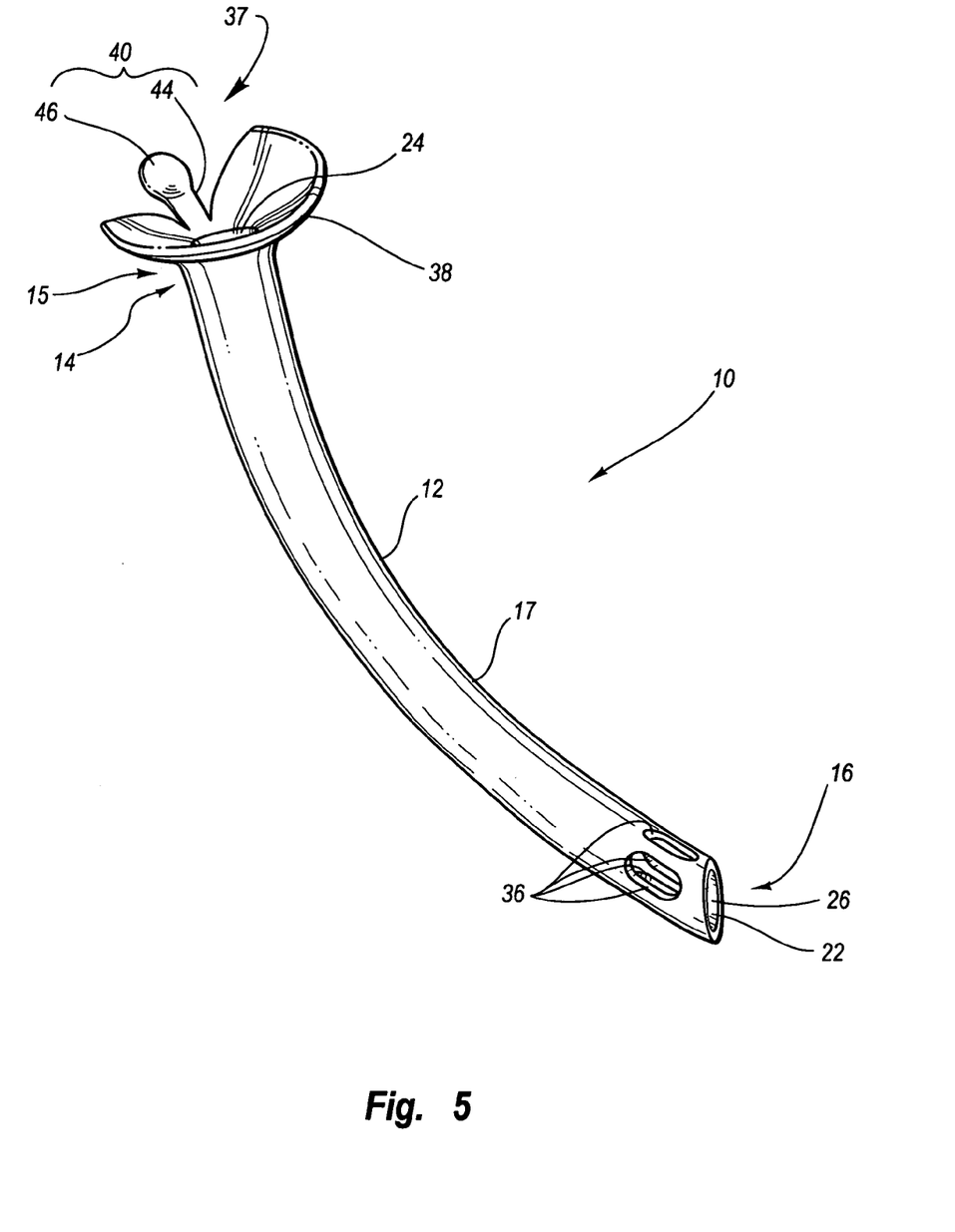
FIGS. 5 and 6 are perspective views of alternative embodiments of the nasopharyngeal airway device shown in FIG. 1.

With reference now to FIG. 5, another embodiment of apertures 36 is illustrated. As shown in FIG. 5, a plurality of apertures 36, such as two, three, or more, are formed at the distal end 16 of tubular body 12. Apertures 36 radially encircle tubular body 12 and communicate with air passage 22. Apertures 36 perform substantially the same function as described above. That is, apertures 36 assist in humidifying the nasal passageway 64 to provide comfort to the patient and help prevent obstruction of air passage 22.

FIG. 6 illustrates yet another embodiment of device 10. FIG. 6 illustrates tip 46 of locking protrusion 40 being formed as a rounded ball. In addition, in FIG. 6 apertures 36 have been maximized along the length of tubular body 12 so as to maximize air flow to lining 68 along nasal passageway 64 (FIG. 4). In this embodiment, apertures 36 are formed as diagonal slots along tubular body 12. In one embodiment, one row of slots is formed on left side 32 of tubular body 12 while an opposing row of slots is formed on right side 34 of tubular body 12. These slots on left side 32 and right side 34 can be configured so that they do not align with each other. In addition, the configuration of apertures 36 may assist to increase the bendability or flexibility of tubular body 12.

In embodiments where apertures 36 may be larger, such as that shown in FIG. 6, reinforcement member 54, as discussed above, can be placed in sidewall 17 of tubular body 12 between apertures 36 to strengthen tubular body 12. Reinforcing members 54 increase the strength of tubular body 12 so as to prevent unwanted collapse or kinking during insertion and use. In addition, reinforcement material 54, for example in the form of reinforcement ribs, may still be disposed on front side 28 or back side 30 of tubular body 12.

In one embodiment of the present invention, means are provided for limiting advancement of tubular body 12 into a nasal passageway. Means are also provided for securing tubular body 12 within the nasal passageway. One example of the means for limiting is flange 38 and the alternatives thereto as discussed above. Once example of the means for securing is locking protrusion 40 and the alternatives thereto as discussed above. Depicted in FIGS. 7–10 are still other embodiments of means for limiting and means for securing.

Figure 7:
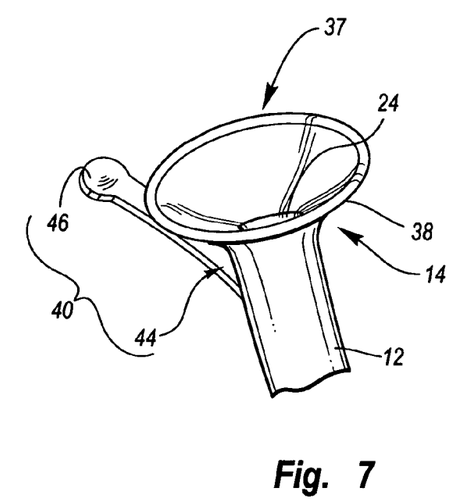
FIGS. 7–10 are perspective views of alternative embodiments of the securement assembly of the nasopharyngeal airway device shown in FIG. 1.

As shown in FIG. 7, flared flange 38 completely encircles tubular body 12 so as to have a substantially frustoconical configuration. Furthermore, FIG. 7 illustrates locking protrusion 40 connected to and extending from tubular body 12. Locking protrusion 40 is still configured to be bent backward into the nasal passageway to secure device 10 thereto. Locking protrusion 40 and flared flange 38 continue to cooperate to form securement assembly 37.

Figure 8:
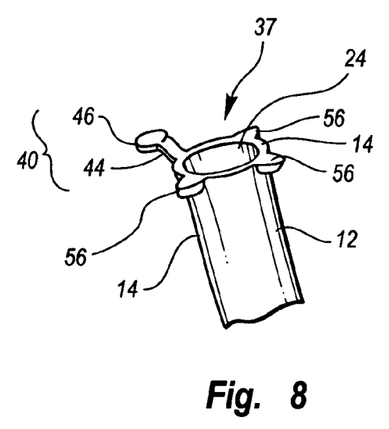

Depicted in FIG. 8, flared flange 38 has been replaced by a plurality of spaced apart flanges 56 that radially outwardly project from proximal end 14 of tubular body 12. Flanges 56 are sized so that proximal end 14 of tubular body 12 cannot freely pass through nostril opening 62. As such, flanges 56 still function to limit advancement of tubular body 12 into nasal passageway 64. Locking protrusion 40 is also shown projecting directly from proximal end 14 of tubular body 12.

Figure 9:
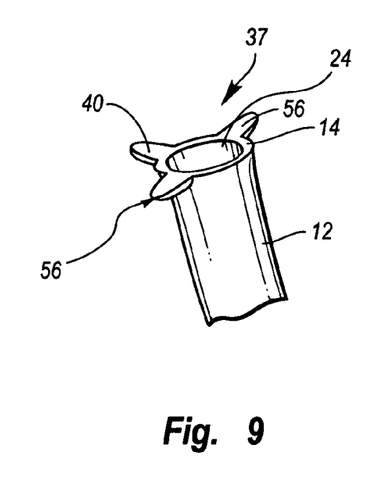

Turning to FIG. 9, it is appreciated that locking protrusion 40 can have substantially the same configuration as flanges 56. That is, locking protrusion 40 need not have an enlarged rounded head formed on the end thereof.

Figure 10:
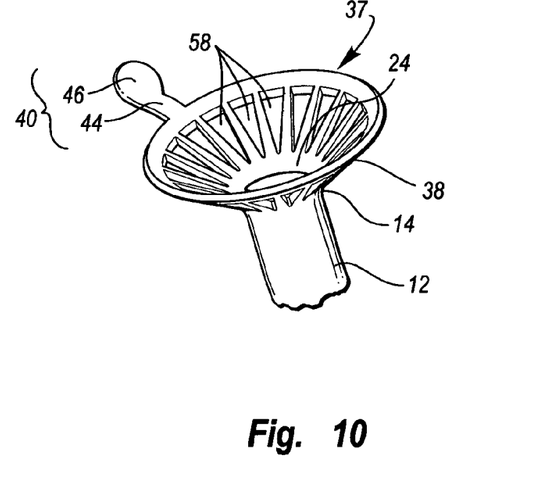

Finally, as shown in FIG. 10, flared flange 38 may include a plurality of apertures 58 extending therethrough. Locking protrusion 40 can also extend from flared flange 38 and perform the same function as discussed above. Flared flange 38 and protrusion 40 continue to cooperate to form securement assembly 37.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A nasopharyngeal airway device configured to be placed within a nasal passageway of a patient, the device comprising:
    a tubular body having an interior surface extending between a proximal end and an opposing distal end, the interior surface at least partially bounding an air passage, the tubular body being adapted to be received within a nostril of a nasal passageway; and
    a securement assembly disposed at the proximal end of the tubular body, the securement assembly comprising:
        a flange that outwardly projects from the proximal end of the tubular body; and
        a flexible elongated locking protrusion having a proximal end and an opposing distal end, the proximal end of the locking protrusion being fixed to either the flange or the proximal end of the tubular body, and the distal end of the locking protrusion terminating at a tip, the locking protrusion being configured such that at least the tip of the locking protrusion is disposed within the same nostril of the nasal passageway as the nostril in which the tubular body is disposed when the tubular body is disposed within the nasal passageway and at least a portion of the flange is disposed outside of the nasal passageway.

2. The device as recited in claim 1, wherein the flange completely encircles the proximal end of the tubular body.

3. The device as recited in claim 2, wherein the flange has a frustoconical configuration.

4. The device as recited in claim 1, wherein the flange encircles at least half of the proximal end of the tubular body and outwardly projects therefrom.

5. The device as recited in claim 1, further comprising a plurality of spaced apart flanges that outwardly project from the proximal end of the tubular body.

6. The device as recited in claim 1, wherein the elongated locking protrusion projects from the flange.

7. The device as recited in claim 1, wherein the elongated locking protrusion projects from the tubular body.

8. The device as recited in claim 1, wherein the tip of the elongated locking protrusion is rounded.

9. The device as recited in claim 8, wherein the tip of the elongated locking protrusion comprises a rounded ball.

10. The device as recited in claim 1, further comprising a reinforcing member connected to and extending between the tubular body and the elongated locking protrusion.

11. The device as recited in claim 10, wherein the reinforcing member comprises at least one fiber embedded within the tubular body and the elongated locking protrusion.

12. The device as recited in claim 1, wherein the elongated locking protrusion is comprised of plastic, rubber, silicone, foamed polymer or a combination thereof.

13. The device as recited in claim 1 wherein the tubular body is comprised of a first material and the elongated locking protrusion is comprised of a second material, the second material being different than the first material.

14. The device as recited in claim 1, further comprising a reinforcing member disposed along the length of the tubular body.

15. The device as recited in claim 1, further comprising a plurality of spaced apart openings extending through the tubular body so as to communicate with the air passage.

16. The device as recited in claim 15, wherein the plurality of openings are disposed at the distal end of the tubular body and are radially spaced apart.

17. The device as recited in claim 15, wherein the plurality of openings are longitudinally spaced apart along the length of the tubular body.

18. A nasopharyngeal airway device configured to be placed within a nostril of a nasal passageway of a patient, the device comprising:
    a tubular body having an interior surface extending between a proximal end and an opposing distal end, the interior surface at least partially bounding an air passage;
    means for limiting advancement of the tubular body into a nostril of the nasal passageway, the means for limiting being disposed at the proximal end of the tubular body; and
    means for securing the tubular body within the nasal passageway, the means for securing being elongated and projecting from the means for limiting and at least a portion of the means for securing biasing against a lining of the same nostril of the nasal passageway as the nostril in which the tubular body is disposed during use.

19. The device as recited in claim 18, wherein the means for limiting comprises at least one flange outwardly projecting from the proximal end of the tubular body.

20. The device as recited in claim 18, wherein the means for securing comprises an elongated, flexible locking protrusion projecting at the proximal end of the tubular body.

21. The device as recited in claim 20, wherein the locking protrusion projects from the tubular body or the means for limiting.

22. The device as recited in claim 20, further comprising a reinforcing member connected to and extending between the tubular body and the locking protrusion.

23. The device as recited in claim 18, further comprising a plurality of spaced apart openings extending through the tubular body so as to communicate with the air passage.

24. The device as recited in claim 23, wherein the plurality of openings are disposed at the distal end of the tubular body and are radially spaced apart.

25. The device as recited in claim 23, wherein the plurality of openings are longitudinally spaced apart along the length of the tubular body.

26. A nasopharyngeal airway device configured to be placed within a nasal passageway of a patient, the device comprising:
   a tubular body having an interior surface extending between a proximal end and an opposing distal end, the interior surface at least partially bounding an air passage, the tubular body being adapted to be received within a nostril of a nasal passageway; and
   a securement assembly disposed at the proximal end of the tubular body, the securement assembly comprising:
      a flange tat outwardly projects from the proximal end of to tubular body; and
      a locking protrusion comprising a flexible elongated stem terminating at a tip, the locking protrusion being configured such that at least the tip of the stem can be is disposed within the same nostril of the nasal passageway as the nostril in which the tubular body is disposed when the tubular body is disposed within the nasal passageway and at least a portion of the flange is disposed outside of the nasal passageway.

27. The device as recited in claim 26, wherein an enlarged rounded structure is formed at the tip of the elongated stem.

28. The device as recited in claim 27, wherein the elongated stem projects from the tubular body.

29. The device as recited in claim 1, wherein the tubular body and the securement assembly are simultaneously molded as a unitary member.

30. The device as recited in claim 1, wherein the flexible locking protrusion comprises an elongated stem formed from a resiliently flexible material such that when the elongated stem is bent over along a length thereof, the elongated stem resiliently returns to a resting state.

* * * * *

UNITED STATES PATENT AND TRADEMARK OFFICE
CERTIFICATE OF CORRECTION

PATENT NO. : 7,100,612 B2
APPLICATION NO. : 10/936940
DATED : September 5, 2006
INVENTOR(S) : Ivan L. Dunlap It is certified that error appears in the above-identified patent and that said Letters Patent is hereby corrected as shown below:

Column 1
Line 17, change "devices" to --device--
Line 19, change "devices" to --device--
Line 37, change "patient'S" to --patient's--
Line 52, change "patent" to --patient--
Line 56, change "that ability" to --the ability--

Column 3
Line 16, change "included" to --include--
Line 67, change "into nasal" to --into the nasal--

Column 4
Line 24, change "show" to --shown--
Line 26, change "comprises" to --comprise--
Line 56, change "stern" to --stem--
Line 65, change "30" to --38--
Line 67, change "61" to --62--

Column 5
Line 9, change "30" to --38--
Line 30, change "comprises" to --comprise--
Line 34, after "locking protrusion" insert --40--
Line 42, change "an trauma" to --trauma--

Column 6
Line 6, after "Reinforcing member" add --54--
Line 8, after "reinforcing member" add --54--
Line 21, change "can comprised" to --can be comprised--

Column 9
Line 17, change "a flange tat" to --a flange that--
Line 18, change "to" to --the--

UNITED STATES PATENT AND TRADEMARK OFFICE
CERTIFICATE OF CORRECTION

PATENT NO. : 7,100,612 B2
APPLICATION NO. : 10/936940
DATED : September 5, 2006
INVENTOR(S) : Ivan L. Dunlap It is certified that error appears in the above-identified patent and that said Letters Patent is hereby corrected as shown below:

Column 10
Line 2, change "can be is disposed" to --can be disposed--

Signed and Sealed this

Seventh Day of August, 2007

JON W. DUDAS
*Director of the United States Patent and Trademark Office*